(12) United States Patent
Wendel et al.

(10) Patent No.: US 12,020,790 B1
(45) Date of Patent: *Jun. 25, 2024

(54) INTELLIGENT MULTI-PARTY REMOTE CARE SYSTEM

(71) Applicant: WALGREEN CO., Deerfield, IL (US)

(72) Inventors: Peter Wendel, Saint Joseph, MI (US); Teresa L. Stumreiter, Lisle, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,685

(22) Filed: Apr. 14, 2023

Related U.S. Application Data

(63) Continuation of application No. 16/743,993, filed on Jan. 15, 2020, now Pat. No. 11,646,106.

(51) Int. Cl.
G16H 15/00 (2018.01)
G06Q 30/0226 (2023.01)
G06Q 30/0601 (2023.01)
G10L 15/00 (2013.01)
G10L 15/08 (2006.01)
G16H 80/00 (2018.01)
G06Q 30/0207 (2023.01)

(52) U.S. Cl.
CPC ......... *G16H 15/00* (2018.01); *G06Q 30/0232* (2013.01); *G06Q 30/0621* (2013.01); *G10L 15/00* (2013.01); *G10L 15/08* (2013.01); *G16H 80/00* (2018.01); *G06Q 30/0207* (2013.01)

(58) Field of Classification Search
CPC ...... G16H 15/00; G16H 80/00; G06Q 30/232; G06Q 30/0621; G06Q 30/0207; G10L 15/00; G10L 15/08

USPC .......... 705/3; 704/231; 379/201.01
See application file for complete search history.

(56) References Cited

U.S. PATENT DOCUMENTS

| | | | | |
|---|---|---|---|---|
| 8,412,537 | B1 * | 4/2013 | Fenton | G16H 10/60 705/2 |
| 11,715,467 | B2 * | 8/2023 | Lefkofsky | G16H 70/20 705/3 |
| 2002/0059081 | A1 * | 5/2002 | Yasuda | G16H 15/00 705/3 |
| 2009/0113008 | A1 * | 4/2009 | Gonzalez | G16H 20/00 709/206 |
| 2012/0011242 | A1 | 1/2012 | Suchter et al. | |
| 2012/0278104 | A1 * | 11/2012 | Traughber | H04M 1/72409 705/2 |

(Continued)

OTHER PUBLICATIONS

Walgreens Smartphone App., URL: https://www.walgreens.com/topic/mobile/apps/learn_about_mobile_apps.jsp, accessed Apr. 14, 2020.

(Continued)

*Primary Examiner* — William J Deane, Jr.
(74) *Attorney, Agent, or Firm* — MARSHALL, GERSTEIN & BORUN LLP; Randall G. Rueth

(57) ABSTRACT

In a method for sharing health care information, a computing system of a care receiver receives first data, including a voice message, from a computing system of a caregiver. Based on the first data, the care receiver's computing system determines a notification time associated with the voice message. The care receiver's computing system causes a speaker to generate the voice message at the notification time.

20 Claims, 6 Drawing Sheets

(56) References Cited

U.S. PATENT DOCUMENTS

| | | | |
|---|---|---|---|
| 2015/0254416 A1* | 9/2015 | Shih | G16H 80/00 |
| | | | 705/2 |
| 2015/0348396 A1 | 12/2015 | Sattari | |
| 2016/0267247 A1 | 9/2016 | High et al. | |
| 2016/0284202 A1* | 9/2016 | Traughber | G16H 80/00 |
| 2017/0124276 A1 | 5/2017 | Tee | |
| 2018/0271753 A1 | 9/2018 | Joyce et al. | |
| 2019/0318283 A1* | 10/2019 | Kelly | G06Q 10/1095 |
| 2020/0064981 A1* | 2/2020 | Uenohara | G06F 3/0486 |
| 2020/0176130 A1* | 6/2020 | Kustra | G16H 40/63 |
| 2020/0349328 A1* | 11/2020 | Espinosa | G06K 7/10297 |
| 2021/0057095 A1 | 2/2021 | Dunstan et al. | |
| 2021/0090694 A1* | 3/2021 | Colley | G16H 15/00 |
| 2021/0133509 A1 | 5/2021 | Wall et al. | |

OTHER PUBLICATIONS

Shopping List Voice Input Android App from T.K. Solution, URL: https://play.google.com/store/apps/details?id=com.tksolution.einkaufszettelmitspracheingabe&hl=en_US, accessed Apr. 14, 2020.

\* cited by examiner

INTELLIGENT MULTI-PARTY REMOTE CARE SYSTEM

CROSS-REFERENCE TO RELATED APPLICATIONS

This is a continuation of U.S. patent application Ser. No. 16/743,993, filed on Jan. 15, 2020, the entire disclosure of which is hereby incorporated herein by reference in its entirety.

FIELD OF THE DISCLOSURE

This disclosure relates to systems and methods that facilitate administration and/or procurement of medication, physical therapy, exercise and/or other healthy habits.

BACKGROUND

Communication between a busy caregiver and a remotely located care receiver, such as between an adult and an elderly parent, can be difficult in the best of circumstances. Care receivers often need reminders to take medication, perform physical therapy exercises, or perform other healthy habits on a regular basis. For example, failure to adhere to medication instructions or a therapy regimen may adversely affect the care receiver's health. In addition, care receivers can have varying levels of memory loss or dementia, which make it difficult to remember to take such actions.

Moreover, caregivers may be busy and distracted, and may forget to remind the care receiver of his or her regular medication, exercise or other healthy habits (or may remember to do so only at inappropriate times, e.g., well before the care receiver needs to take his or her medication). The caregiver, especially when remotely located, may also have trouble assessing the needs of the health receiver. Caregivers may also want a greater level of confidence that the care receiver is taking the necessary medications, or otherwise addressing his or her health needs.

Care receivers may additionally lack the ability to navigate email or two-way text messaging to ask for help or indicate a need, such as help for a new health condition, or a need to refill a medication, etc.

At the same time, health care entities (e.g., pharmacies, hospitals, etc.) may wish to collect more useful customer data, and/or make better use of such data to assist the health care receiver.

SUMMARY

Systems and techniques of this disclosure deliver a caregiver's recorded voice to a computing system (e.g., a Google Home® voice-controlled smart speaker or other device) of a remote care receiver, at notification times indicated by the caregiver. The disclosed methods and systems also enable the care receiver to deliver a voice response to the caregiver. The computing system of the caregiver and/or the computing system of the care receiver could be a traditional home computer, a cellular smartphone, a Google Home® voice-controlled smart speaker, or any other suitable computing device or system with at least one speaker and at least one microphone.

A smart speaker system with voice recognition may be especially important for the care receiver, who may be unable to answer queries with a keyboard. A fully abled caregiver may also prefer the convenience of a smart speaker system, or may prefer the mobility of a smartphone. Smartphone use by a caregiver may also provide other advantages for the caregiver, such as delivery of a health care shopping list for the care receiver (e.g., with recognized or predicted health care items including marketing and/or medicinal items, as discussed in further detail below), at a time when the caregiver is near an appropriate location such as a pharmacy.

Initially, the caregiver uses his/her computing system to record a voice message, which includes a personalized reminder for the care receiver, and optionally also an indication of a notification time and/or a message expire time. The computing system of the caregiver then delivers the voice message to the computing system of the care receiver at the indicated notification time (or a default notification time). In one embodiment, the computing system of the care receiver holds the message until the indicated or default notification time, and plays back the message for the care receiver at that notification time. In other embodiments, the computing system of the caregiver forwards the voice message with an associated notification time to a computing system of a third party health care entity, which holds the voice message until the notification time. The computing system of the health care entity then forwards the voice message to the computing system of care receiver at the notification time, after which the care receiver's computing system immediately performs playback of the message for the care receiver. Alternately, the computing system of the health care entity may immediately forward the voice message to the computing system of the care receiver along with an indication of the notification time, after which the computing system of the care receiver holds the message for playback at the indicated notification time.

After playback of the recorded voice message, the care receiver's computing system monitors for the care receiver's voice response using a microphone of his or her computing system. After receiving the voice response, the computing system of the care receiver sends the voice response back to the computing system of the caregiver (e.g., the caregiver's smartphone or another smart speaker, etc.).

In this manner, the care receiver generates a voice response to the caregiver's reminder voice message to confirm to the caregiver that a medicine has been administered or an exercise has been performed. If the care receiver cannot respond, this may indicate to the caregiver that a more urgent health problem exists. The computing system of the care receiver may notify the computing system of the caregiver or notify emergency personnel (e.g., trigger an alarm) if care receiver's computing system did not receive a response from the health care receiver (e.g., before expiration of the message expire time). This message expire time can be default for all voice messages, or can be included in or with the voice message.

In some embodiments that include connectivity through a computing system (e.g., a server or servers) of a health care entity, the entity may provide merchandise availability information, digital coupons and/or other marketing information. Medicinal information such as drug refill status, prescription pricing, copay costs, estimated prescription fill time, vaccine reminders or other medicinal information may also be referenced by the health care entity and included in the messaging. The sharing of this data assumes that the proper privacy regulations are followed and that the proper Health Insurance Portability and Accountability Act (HIPAA) authorization has previously been received by the health care entity as an "opt-in" from the health care receiver or the receiver's legal representative. The entity may determine the marketing or medicinal information directly from voice messages passed between the particular care receiver and the caregiver (e.g., if the care receiver mentions a particular product that he or she needs), or based upon a predicted need for particular items (e.g., based on the care receiver mentioning certain ailments, and/or using a history of the items purchased for and/or used by the care receiver). In some embodiments, the entity may produce a list of suggested items based on the voice data and past purchases of other care receivers. With past purchase information from other individuals (e.g., other care receivers), the entity may use machine-learning techniques to predict a list of other needs of the particular care receiver. For example, a high percentage of individuals that purchase diabetes supplies may also purchase isopropyl alcohol pads. Thus, the entity may add isopropyl alcohol pads to a machine-learning list of predictions for a care receiver whose voice messages indicated that he or she is out of some other diabetes testing supply.

The systems and techniques of this disclosure use recorded voice messages and message timing mechanisms to facilitate the job of the caregiver, and more consistently satisfy the care receiver's needs. Moreover, supervised machine-learning and other techniques allow the health care entity to better address the care receiver's needs with accessible, timely and useful data, assuming that all applicable transparency and privacy laws and regulations are satisfied.

DETAILED DESCRIPTION

This detailed description is to be construed as exemplary only and does not describe every possible embodiment, which would be impractical. Numerous alternative embodiments could be implemented, using either current technology or technology developed after the filing date of this patent, which would still fall within the scope of the claims.

Figure 1:
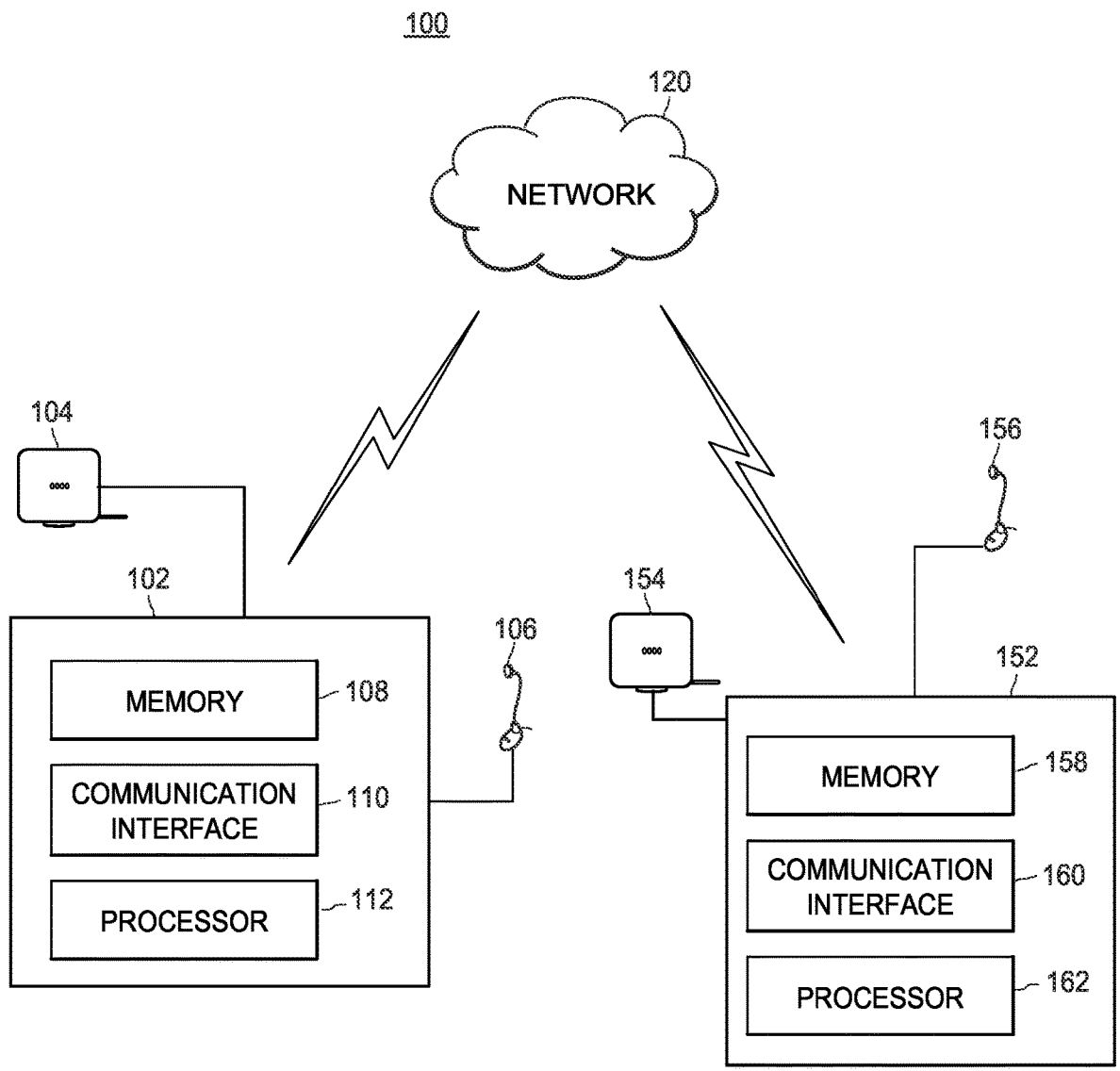
FIG. 1 illustrates an example peer-to-peer configuration in which caregiver and care receiver computing systems are connected via a network.

FIG. 1 illustrates a peer-to-peer configuration 100 that includes a caregiver computer system 102 connected via a network 120 to a care receiver computer system 152. The network 120 may include one or more networks of any suitable type or types, such as the Internet and possibly an Ethernet using any of several Transmission Control Protocols (TCP) or User Datagram Protocols (UDP). The caregiver computer system 102 includes a memory 108 and/or other non-transitory computer-readable storage media (also referred to herein as simply "memory 108"), one or more processors 112 (also referred to herein as simply "processor 112"), a communications interface 110, a one or more microphones 106 (also referred to herein as "microphone 106"), and one or more speakers 104 (referred to herein as "speaker 104"). The microphone 106 may be, for example, an omnidirectional condenser microphone that sits on a desktop (with wired or wireless connectivity to the remainder of the computing system 102), a microphone built into a smart speaker product, or a microphone built into a smartphone. The speaker 104 may be included as part of a smart speaker system such as a Google Home® product, external to a home computer, or built into a smartphone, for example. The processor 112 may include one or more central processing units (CPUs) and/or graphics processing units (GPUs), for example. The memory 108 may include one or more volatile and/or non-volatile memories (e.g., a hard drive and/or solid-state memory, RAM, ROM, PROM, EPROM, flash memory, and/or other non-transitory computer-readable storage media). The processor 112 executes instructions that are stored in the memory 108.

The communication interface 110 includes hardware, software and/or firmware configured to send data over the network 120. For example, the communication interface 110 may include one or more units that support a TCP protocol (e.g., HTTP, HTTPs, SMTP, SMPP, Telnet), a UDP protocol (e.g., Voice over Internet Protocol), and/or one or more other protocols (e.g., IEEE 802.11 (Wi-Fi) protocol, cellular protocol (e.g., LTE, 5G), etc.). Similarly, the computing system 152 of the care receiver includes a memory 158. The memory 158 may include one or more volatile and/or non-volatile memories (e.g., a hard drive and/or solid-state memory, RAM, ROM, PROM, EPROM. flash memory) and/or other non-transitory computer-readable storage media (referred to herein as simply "memory 158"), one or more processors 162 (also referred to herein as "processor 162"), a communication interface 160, one or more microphones 156 (also referred to herein as "microphone 156"), and one or more speakers 154 (referred to herein as "speaker 154"). The memory 158, processor 162, communication interface 160, microphone 156 and/or speaker 154 may be the same as or similar to the memory 108, processor 112, communication interface 110, microphone 106 and/or speaker 104, for example.

Generally, the care receiver's computing system 152 and caregiver's computing system 102 may be any suitable type of computing device or system, such as a smart speaker device with integrated components (e.g., Google Home®), a cellular smartphone, an Internet-enabled tablet, and so on. In some embodiments, the computing systems 102 and 104 are of different types. In one embodiment, for example, the caregiver computing system 102 is a smartphone, while the care receiver computing system 152 is a smart speaker device.

The memory 108 in the caregiver's computing system 102 stores instructions that, when executed by the processor 112, cause the computing system 102 to detect (via the microphone 106) and digitally record (e.g., in a different portion or unit of the memory 108) a voice message of the caregiver. The voice message may be words that the caregiver speaks to remind the care receiver of a health-related task (e.g., a reminder to take medication or make an appointment), or may be another type of health-related message intended for the care receiver. The caregiver may also choose to indicate an explicit notification time for the reminder (or other message), using his or her voice or by other means, such as a keyboard. Alternately, the caregiver may trigger a default time (e.g., immediate delivery) of the message by not specifying a time.

In some embodiments, the computing system 102 determines the notification time indicated by the caregiver (e.g., using speech recognition techniques, or by identifying a time that the caregiver entered via a keyboard, etc.). In other embodiments, as discussed further below, a computing system other than computing system 102 (e.g., the computing system 152 or an intermediary server) determines the notification time. In embodiments where the computing system 102 determines the notification time provided by the caregiver, and/or where the caregiver separately enters the notification time (e.g., via keyboard), the processor 112 associates or packages the caregiver's voice message with the notification time into "first data" (e.g., as discussed further below with reference to FIG. 4), and causes the communication interface 110 to send the first data to the computing system 152 of the care receiver via the communication interface 110 and the network 120. In other embodiments, where the caregiver speaks the notification time but the computing system 102 does not use speech recognition, the processor 112 may send data representing the voice message provided by the caregiver to the computing system 152, without attaching a separate notification time.

After the care receiver's computing system 152 receives the first data from the network 120 via the communication interface 160, the processor 162 extracts the voice message. In embodiments where the first data does not separately include a notification time (e.g., if that time was not determined/identified in the voice message by computing system 102 or any intervening server), the processor 162 may use speech recognition techniques to determine the notification time. The processor 162 then causes the speaker 154 to generate the voice message at the indicated notification time. As noted above, in some embodiments, the computing system 152 may immediately generate the voice message if the first data did not include an associated notification time, and/or if the computing system 152 is unable to identify a notification time by applying speech recognition techniques.

After hearing the voice message, the care receiver may choose to respond to the voice message with a voice response. The memory 158 in the care receiver's computing system 152 stores instructions that, when executed by the processor 162, cause the computing system 152 to listen/monitor for (via the microphone 156) a voice response message of the care receiver, and to digitally record that message (e.g., in a different portion or unit of the memory 158) when detected by the computing system 152. The computing system 152 sends "second data," including the voice response message, back to the computing system 102 of the caregiver, via the communication interface 160 and the network 120.

In some embodiments, if the care receiver does not respond before a predetermined time (e.g., before expiration of a timer implemented by the processor 162), or if the care receiver does not respond before a period of time equivalent to a message expiration time parameter that is included in the first data (automatically, or in response to a parameter entered by the caregiver via keyboard, etc.), the computing system 152 of the care receiver generates alarm data. The computing system 152 may send the alarm data to the computing system 102 of the caregiver to trigger an alarm (e.g., via the speaker 104 and/or a display of the computing system 102), for example. The alarm data may be in the format required by Simple Network Management Protocol (SNMP) or another suitable protocol, for example. Alarm data may also comprise data or text included in a message to the caregiver's smartphone such as in a Short Message (SMS) or Multi-Media Message (MMS), a secure Over the Top (OTT) messaging application (such as WhatsApp® or other OTT Instant Message software) or an Application Programming Interface (API) call to an additional software application, for example. In addition to being sent to the computing system 102 of the caregiver, the alarm data may be sent by the computing system 152 of the care receiver to another individual or entity (e.g., a backup caregiver or emergency personnel).

In some embodiments, the alarm data denotes a particular alarm level among two or more possible alarm levels, such that the alarm can escalate as the situation becomes more urgent or dire. For example, if the care receiver does not respond within a first threshold time (e.g., 1 minute) the computing system 152 of the care receiver may generate "Level 1" alarm data, and send the alarm data to the computing system 102 of the caregiver (e.g., to trigger a text or voice notification message to the caregiver). If the care receiver still does not respond within a second, greater threshold time (e.g., 5 minutes), the computing system 152 may generate and send "Level 2" alarm data (e.g., to trigger a louder or otherwise more urgent notification for the caregiver, etc.). In some embodiments, alarms can also, or instead, be escalated by lack of acknowledgment from the caregiver. For example, the computing system 152 may instead generate the "Level 2" alarm data if the system 152 does not receive a responsive voice message from the computing system 102 of the caregiver (or receive some other kind of confirmation from the system 102) within some threshold amount of time. Alternatively, the computing system 102 may generate the "Level 2" alarm data in response to failing to detect a responsive caregiver voice message within the threshold time. In either case, the computing system generating the alarm data (system 152 or 102) may then send the "Level 2" alarm data to the computing system of a backup caregiver and/or emergency personnel, for example.

Figure 2:
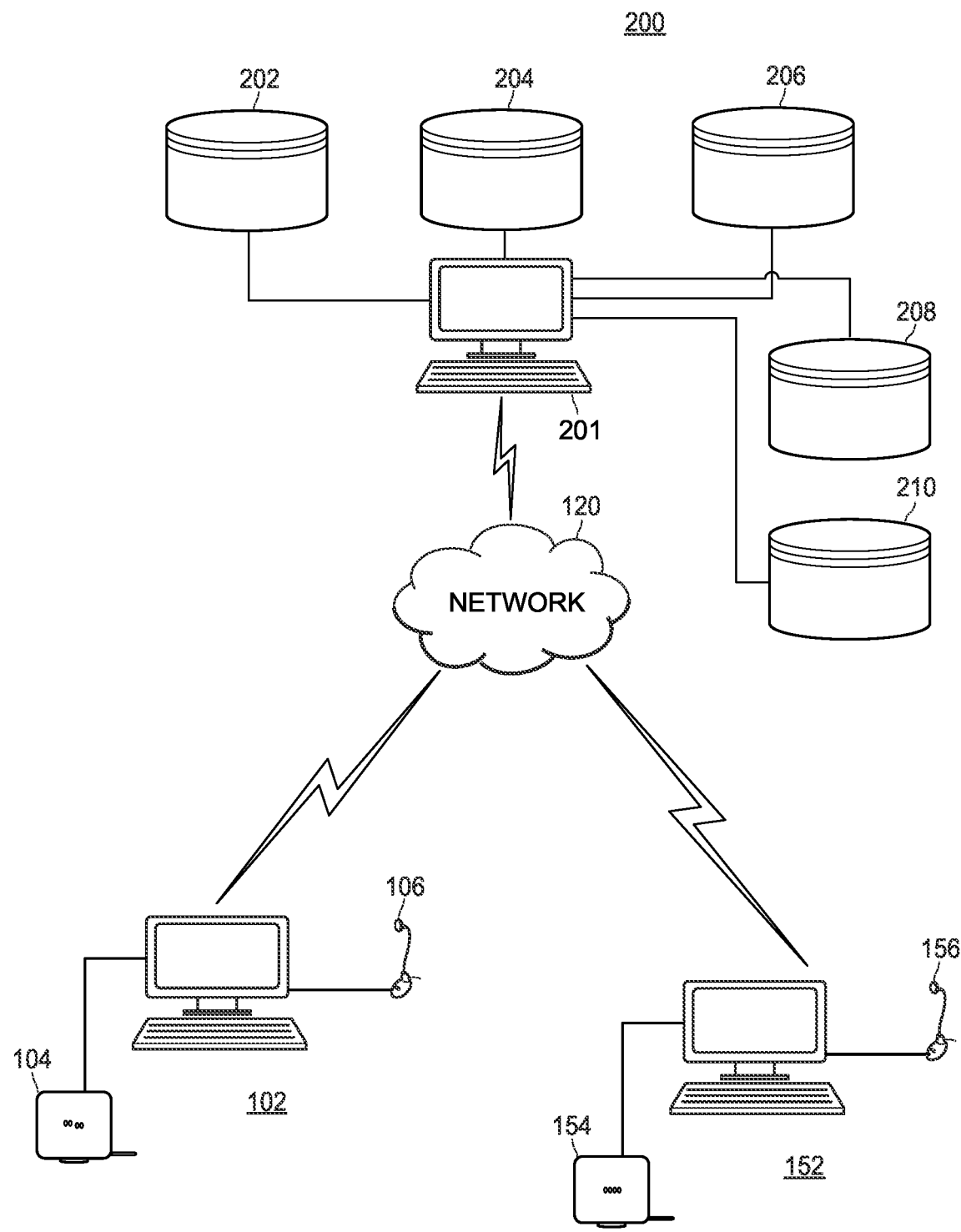
FIG. 2 illustrates a configuration in which care receiver, caregiver and health care entity computing systems are connected via the network.

FIG. 2 illustrates another example configuration 200 in which the computing systems 102, 152 of the caregiver and care receiver communicate via a health care entity computing system 201. The health care entity may be a health care provider (e.g., a hospital, medical or dental office, etc.), a pharmacy, a health or life insurance company, a vendor of medical supplies, or any other type of entity that may operate partially or exclusively within the field of health care. Components shown in FIG. 2 that have reference numbers previously used in FIG. 1 (e.g., 102, 152, etc.) may be identical to the corresponding components discussed above with reference to FIG. 1. The depicted components of the health care entity computing system 201 (i.e., 202, 204, 206, 208, 210) are described below with reference to FIG. 3. As seen in FIG. 2, the health care entity computing system 201 is communicatively coupled to both the caregiver computing system 102 and the care receiver computing system 152 via the network 120.

Figure 3:
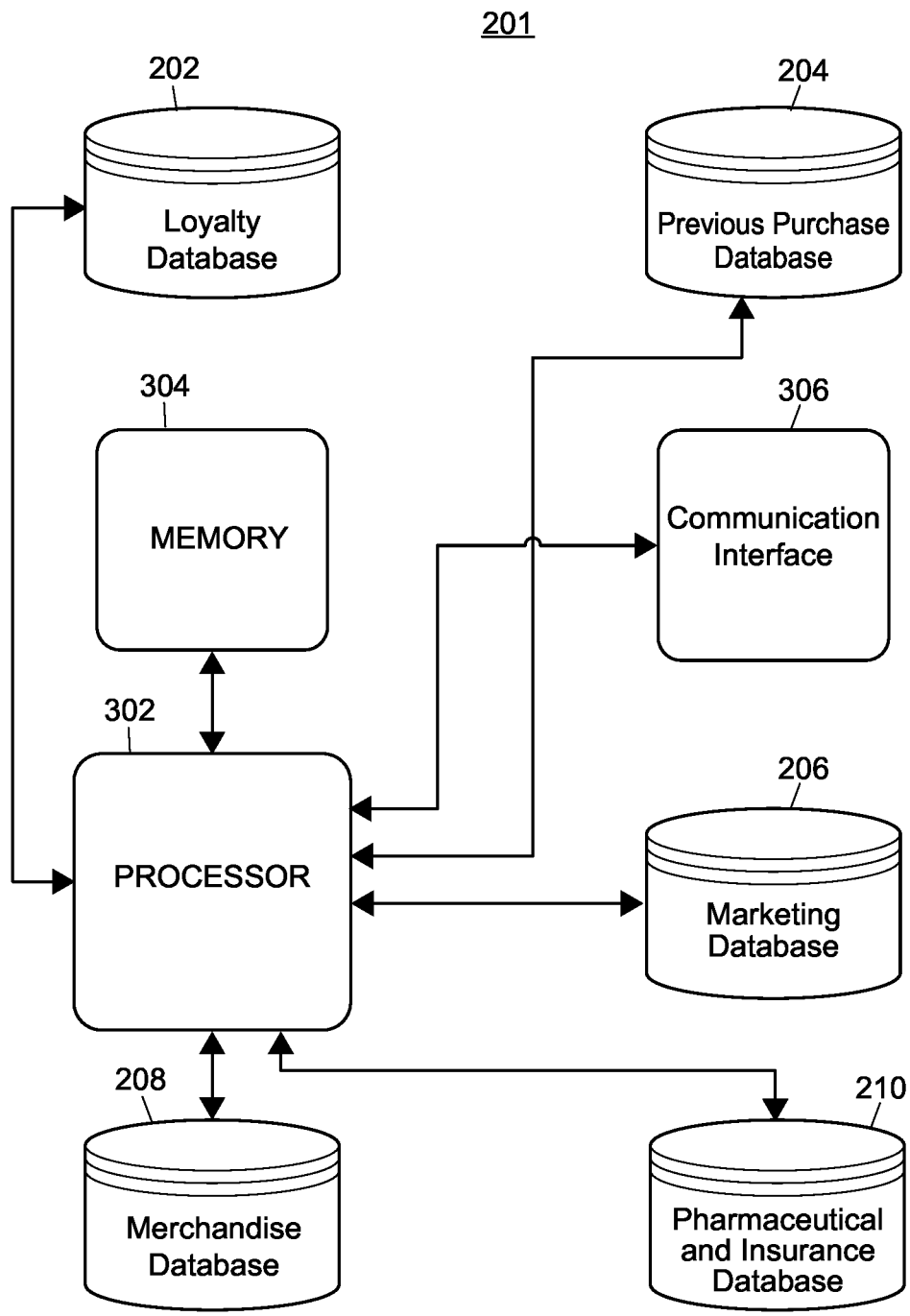
FIG. 3 illustrates an example implementation of the health care entity computing system of FIG. 2.

FIG. 3 illustrates more details of the computing system 201 of the health care entity, including one or more processors 302 (referred to herein as simply "processor 302"), and one or more memories and/or other non-transitory computer-readable storage media (referred to herein as simply "memory 304"), a communication interface 306, and a number of databases 202, 204, 206, 208, 210. The processor 302 executes instructions that are stored in the memory 304. The processors 302 and memory 304 may reside on one or more servers and/or be part of a cloud deployment. For example, the functionality of the computing system 201 described herein may be provided as a web services platform. Each of databases 202, 204, 206, 208 or 210 may include one or more virtual databases, for example, and may be collocated in a combined database or located remote from the health care entity. In the example of FIG. 3, the databases include a loyalty database 202, a previous purchase database 204, a marketing database 206, a merchandise database 208 and a pharmaceutical and insurance database 210.

The loyalty database 202 may contain, for example, points earned toward a refund such as with Walgreens Balance Rewards® system or may be a database necessary for another customer loyalty system. The previous purchase database 204 generally contains data relating to previous purchases and/or purchase decisions of customers (e.g., purchase histories of customers, and possibly storage of digitized previous caregiver voice messages and digitized previous care receiver voice responses). The marketing database 206 may contain, for example, periodic sale and promotional information as well as digital coupons. Merchandise data stored in database 208 may include inventory information such as the availability of health care items at particular locations of the health care entity, for example. The prescription database 210 comprises medicinal information including one or more of diagnosis information, medication information, refill status, Medical Doctor (MD) contact information, MD preauthorization information, vaccination information, potential drug interaction information, health care appointment information, and/or insurance copay or other insurance information of the care receiver.

In embodiments utilizing the configuration 201, the processor 302 of FIG. 3 receives the first data from the computing system 102 of the caregiver. The first data includes a voice message and, in some embodiments, an associated notification time and/or a message expiration time (e.g., as discussed above and later with reference to FIG. 4). In some embodiments, the notification time is in a digitized voice format that the processor 302 converts to timestamp (e.g., a Universal Time Coordinated (UTC) time stamp) using speech recognition techniques. In other embodiments (e.g., where, as noted above, the computing system 102 determined/identified the notification time), the notification time may already be in a timestamp (e.g., UTC) or other suitable format when received by the computing system 201. In a similar fashion, the message expire time (e.g., the number of seconds to wait for a response before triggering an alarm) may be determined using speech recognition or by identifying a time already associated (by computing system 102) with the first data. Alternately a default notification time and default message expire time may be established at either the computing system 102 of the caregiver or at the computing system 201 of the health care entity. In still other embodiments, as noted above, the care receiver computing system 152 determines (e.g., via speech recognition) the notification time and/or the message expire time.

After the computing system 152 of care receiver receives the first data (discussed in FIG. 4), and the voice message found in the first data is announced at the speaker 154, of the computing system 152 of the care receiver at the appropriate notification time, the computing system 152 of the care receiver then monitors for a response from the care receiver via the microphone 156. If a voice response is received from the care receiver, the voice response is passed back to the computing system 201 of the health care entity with the voice response embedded in a second data (as discussed below in FIG. 5). Once the voice response is received, the computing system 201 of the health care entity forwards the voice response from the system 152 back to the system 102 of the caregiver. If no voice response is detected from the care receiver before the expiration time, alarm data is sent by the system 201 of the health care entity to the system 102 of the caregiver and/or sent to an alternate recipient such as, for example, to emergency personnel.

In embodiments utilizing configuration 200, the voice messages and voice response messages both pass through the system 201 and the messages could be stored for example, in a database, such as the previous purchase database 204. The system 201 may scan the voice messages and voice message responses to determine ways to assist the care receiver, and/or for marketing purposes. In addition to examining the general or specific content of messages (e.g., to identify explicit requests or statements of need by the care receiver, or to infer needs of the care receiver), the system 201 of the health care entity may detect other characteristics, such as how many times (and/or how quickly) a request is repeated, the care receiver's voice intonation and/or volume, and so on. The system 201 can then make a decision to take action (or not take action) accordingly. For example, the system 201 may determine that a raised voice or a repeated request is associated with greater urgency, which may in turn trigger a higher alarm level (as discussed above). As another example, the system 201 may determine that a sarcastic intonation lowers the urgency, or may ignore a sarcastic statement entirely. More generally, the system 201 may analyze a voice message (or multiple voice messages over time) of the care receiver in order to understand the context of his or her statements, and the intent that underlies his or her statements.

The processor 302 of the system 201 of the health care entity may examine one or more voice messages 402 of the caregiver and/or one or more associated voice responses 502 from the care receiver that may be stored in a database of the health care entity such as 204 to identify and/or predict a list of one or more items that may assist the care receiver. For example, the care receiver or caregiver may explicitly request that the health care entity place items on the list, or otherwise name specific items, and the processor 302 may use speech recognition techniques against a voice message or voice response message stored in database 204 to identify those items (and possibly to identify context, such as whether the speaker is requesting those items rather than merely mentioning them for other reasons). Alternately, or in addition, the processor 302 may predict some or all of the items to assist the care receiver based upon the voice message(s), and/or based upon past purchase information of the care receiver or caregiver, or based upon medicinal information of the care receiver, and/or other information. In some embodiments, the computing system 201 implements machine learning techniques to develop the predictive models (e.g., neural networks) based on information such as the previous voice messages and/or purchases of other caregivers and/or other care receivers, which may be stored in 204.

In one example of the processor 302 predicting a care receiver's items, the care receiver may vaguely state, in a voice response message, "My skin is dry." Once the predictive model may determines that the care receiver's skin is dry, the processor 302 or another processor identifies products corresponding to a dry skin condition.

The processor 302 may additionally process the voice message using the predictive model, and determine to offer a coupon for a particular type or brand of skin lotion. As another example, the predictive model may directly predict that the product would be helpful, without first "diagnosing"

a condition. Based on the knowledge that many individuals with dry skin also purchase lip balm, the health care entity may offer a coupon for lip balm or suggest that lip balm is on sale via online purchase or at a nearby location. In yet another example, assuming the proper HIPAA authorization has previously been received by the health care entity, the processor 302 may use the care receiver's known medicinal information. For instance, if the care receiver states, "I'm almost out of my diabetes medicine!" the computing system 201 may notify the caregiver of the best location to pick up the medicine that was previously prescribed to the care receiver. For example, the computing system 201 may notify the computing system 102 of the caregiver: "Metformin in the 500 mg dosage is out of stock at your usual pharmacy, but can be refilled immediately at Walgreens at 811 Madison St. in Oak Park, IL. There is a $5 copay."

After generating a list of one or more health care items, the computing system 201 of the health care entity sends the list to the computing system 102 of the caregiver (or possibly, in another embodiment, to the computing system 152 of the care receiver). In response to receiving the list, the computing system (102 or 152) causes the speaker(s) (104 or 154) to generate a voice message that includes the list of items, and/or causes a display of the receiving computing system to show a text list of the items.

In some embodiments, the computing system 201 may also, or instead, identify appropriate marketing information (e.g., digital coupons, customer loyalty information, sale information, merchandise availability information, etc.) based on the identified or predicted items, and/or may add prescription information to the list.

The processor 302 of the health care entity causes the caregiver's computing system 102 (or, in one embodiment, the computing system 154 of the care receiver) to generate a voice message with the list of these additional items based on information derived from one or more of the databases 202, 204, 206, 208 and 210 shown in FIG. 2 and FIG. 3. The list may be sent to the caregiver via the speaker 104 and/or in text format, such as in a SMS or MMS (e.g., to the caregiver's smartphone). The list may include additional items predicted to assist the care receiver based on past purchase history and/or as determined by a machine-learning method executed on the computing system 201 of the health care entity. The caregiver or care receiver, upon receiving the list, may then authorize online purchase of the listed item(s) with an authorization, such as a voice authorization from the care receiver or a voice or text authorization from the caregiver, for example. The voice or text authorization message may be contained in data that the caregiver computing system 102 or care receiver computing system 152 sends to the health care entity computing system 201 via the network 120.

In some embodiments, the computing system 201 delivers the list to the caregiver when the computing system 201 determines that the caregiver is in the proximity of a point of purchase. To this end, a location-based application resident on the caregiver's smartphone or other mobile device (e.g., computing system 102) may share the location of the caregiver's smartphone or other mobile device with the computing system 201, for example. The computing system 201 may then use the shared location to determine the proximity of the caregiver to a physical location of a pharmacy. When the caregiver is in the proper vicinity, the computing system 201 may send to the caregiver's smartphone or other device a list of health care items (such as medicine) to purchase or refill, and possibly digital coupons or other items on the health care shopping list, for example.

The list may be sent as an SMS, MMS, secure OTT instant message or API interface notification, for example, or via any other suitable means.

Alternatively, the computing system 201 delivers the list to the caregiver regardless of proximity to a particular point of purchase. For example, when the computing system 201 intends to send a list to the caregiver, the system 201 may use the shared location of the caregiver to determine a pharmacy that is currently nearest to the caregiver, to determine a pharmacy that has a particular item in stock and is currently nearest to the caregiver, or to determine directions to a preferred pharmacy of the caregiver. The nearest pharmacy location at any given time may change, for example, as the caregiver moves about for various reasons (e.g., work, errands, etc.).

The processor 302 of the computing system 201 (or another processor and/or computing system) may train a machine-learning model using data drawn from the database 204 of previously purchased items. For example, the training data may include sets of care receiver voice messages (e.g., voice response messages), or certain words included in such messages, etc., paired with labels of one or more health care items that the care receivers desired when forming their respective voice messages (e.g., as indicated by surveys, or by items that were purchased and not returned, etc.). The processor 302 or other processor/system may then use supervised learning techniques to train the model, for example. The processor 302 or other processor/system can then validate the trained machine-learning model using additional data from database 204.

After the model has been trained, the processor 302 can apply the voice message of the caregiver or the voice response message of the care receiver to the model to estimate which item or items may be needed to assist the care receiver. These estimated items are shared with the caregiver and/or the care receiver via messages to their respective computing systems 102, 152, e.g., as discussed above. Purchase of these items can then be authorized in a message to the computing system 201 from the computing system 152 of the care receiver, for example. Alternately, the caregiver could authorize purchase of the items.

Figure 4:
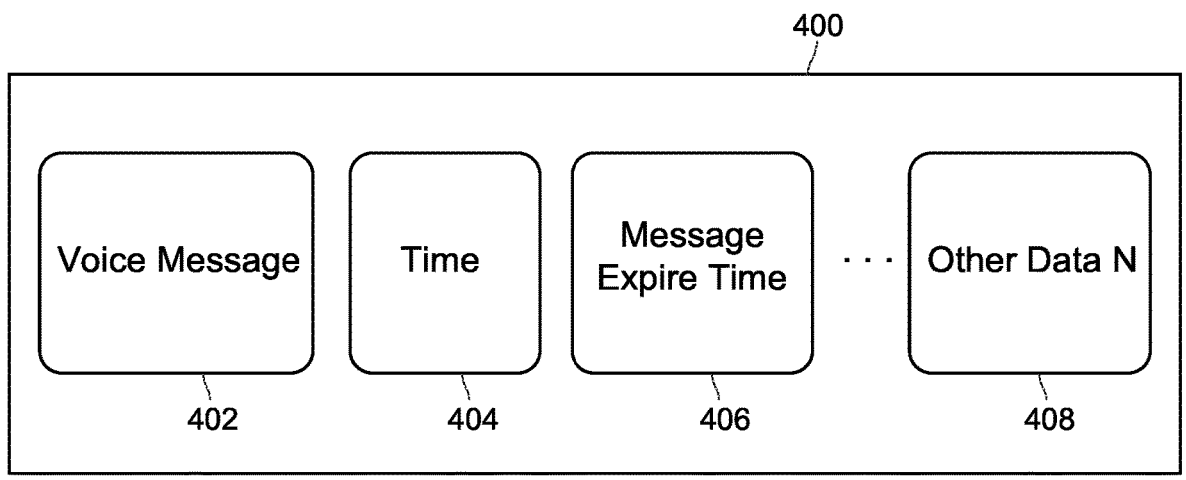
FIG. 4 illustrates example data that the computing system of the caregiver may send to the computing system of the care receiver.

FIG. 4 illustrates an example of the "first data" containing the caregiver's voice message, as discussed above. As seen in FIG. 4, first data 400 comprises a voice message 402 from the caregiver to the care receiver. In the depicted embodiment, the first data 400 also includes a notification time 404. Lack of a notification time may trigger immediate notification, as discussed above. Also optionally included in the first data 400 is a message expire time 406. As discussed above, the message expire time 406 is a time period after which, if the care receiver does not respond, alarm data is sent (e.g., by the computing system 152) to the computing system 102 of the caregiver or to a third party such as an emergency responder. Other parameters 408 of the first data 400 may also be present, and may indicate, for example, to which of several of the care receiver's speakers to send the notification (e.g. bedroom, living room, or an indication of all speakers) or other suitable information.

Figure 5:
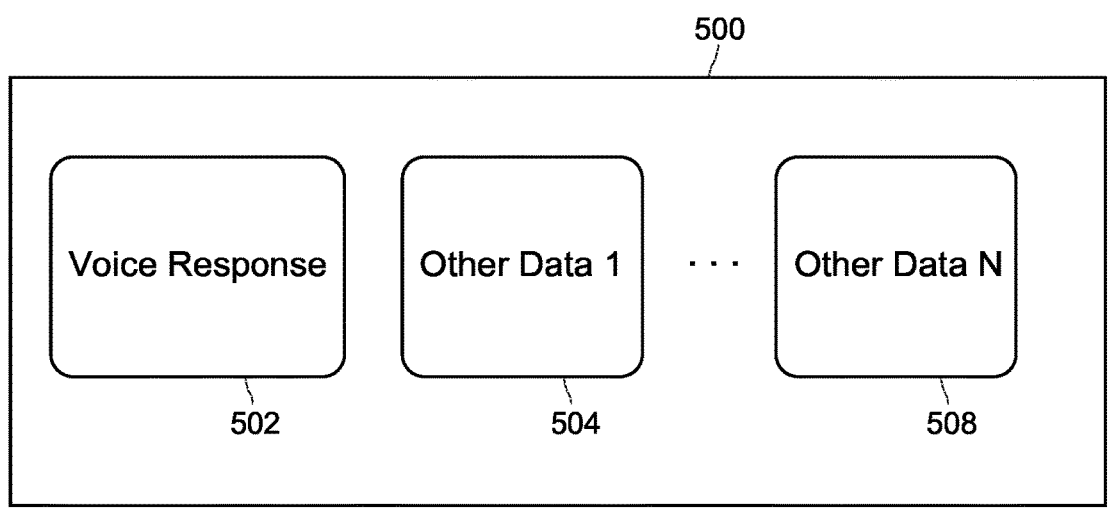
FIG. 5 illustrates example data that the computing system of the care receiver may send to the computing system of the caregiver, after receiving the data of FIG. 4.

FIG. 5 illustrates an example of the "second data" containing the care receiver's voice response message, as discussed above. As seen in FIG. 5, second data 500 includes a voice response message 502 from the caregiver to the care receiver. In some embodiments, the second data 500 also includes other data, such as, for example, the date and/or time when the care receiver provided the voice response message.

Figure 6:
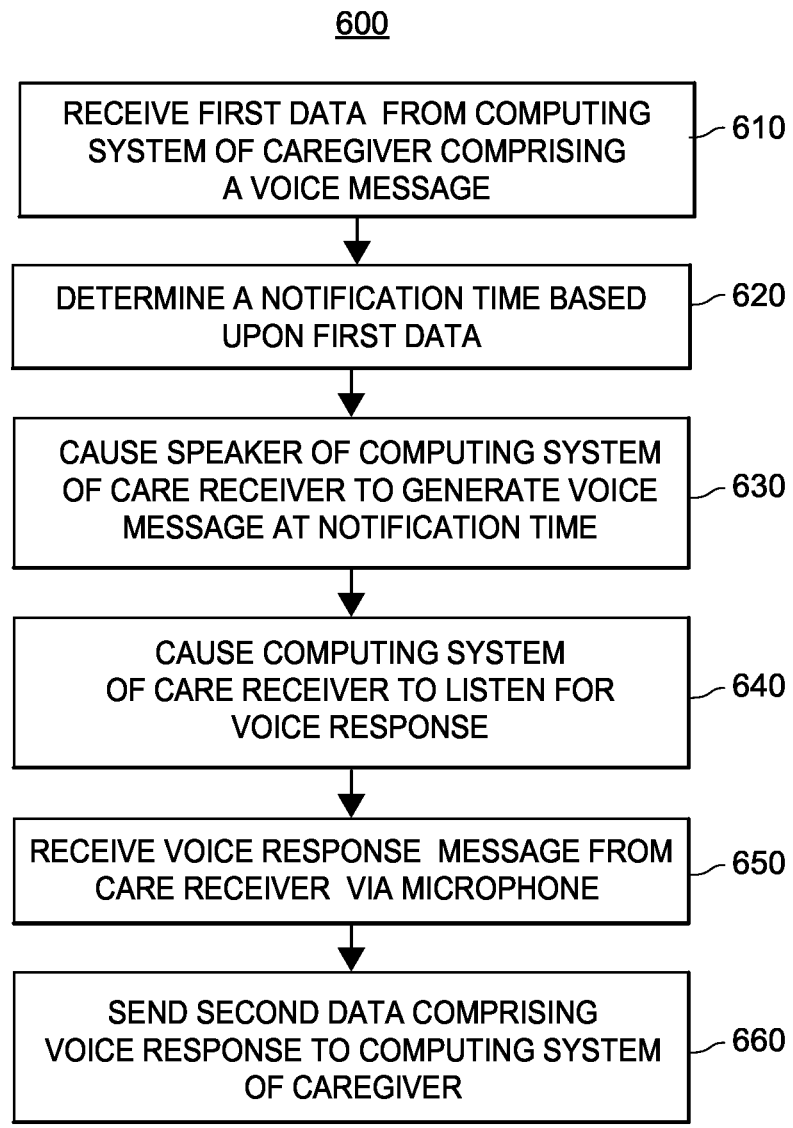
FIG. 6 is a flow chart depicting an example method of sharing health care information, from the perspective of a care receiver's computing system.

FIG. 6 is a flow chart of a method 600 for sharing health care information. The method 600 may be implemented by the computing system of a health care receiver (e.g., the computing system 152 of FIG. 1), for example. At block 610 of the method 600, first data (e.g., the first data 400) containing a voice message is received from a computing system of a caregiver (e.g., from the computing system 102). The first data may be received directly from the caregiver's computing system, or via an intermediary computing system (e.g., the computing system 201 of FIG. 2 and FIG. 3). The first data may be received via a network and communication interface (e.g., the network 120 and the communication interface 160 of FIG. 1), for example.

At block 620, a notification time is determined based upon the first data received at block 610. Block 620 may include using speech recognition techniques to identify a spoken time within the voice message itself or simply identifying a time value in a dedicated field of the first data, for example.

At block 630, a speaker of the care receiver's computing system is caused to generate the caregiver's voice message at the determined notification time. Thereafter, at block 640, the computing system of the care receiver listens for a response from the care receiver. At block 650, the computing system of the care receiver receives a voice response from the care receiver via a microphone (e.g., microphone 156 of FIG. 1). At block 660, the care receiver's computing system uses the network to send second data containing the voice response to the caregiver's computing system either directly, or via the computing system of the health care entity.

Figure 7:
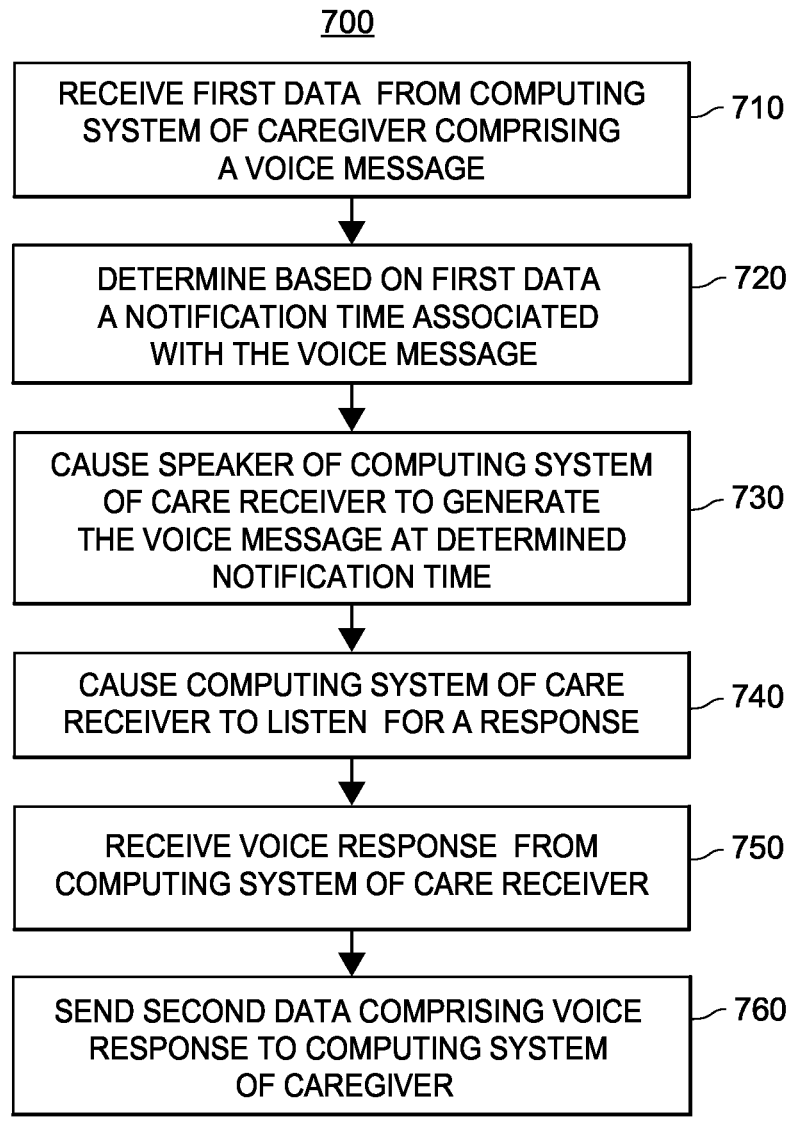
FIG. 7 is another flow chart depicting an example method of sharing health care information, from the perspective of a health care entity's computing system.

FIG. 7 is a flow chart of a method 700 for sharing health care information in a configuration that includes the computing system of a health care entity (e.g., the computing system 201 of FIG. 2 and FIG. 3), with the method 700 being implemented by the computing system of the health care entity. At block 710 of the method, first data (e.g., first data 400) containing a voice message is received from the computing system of a caregiver (e.g., the computing system 102 of FIG. 1).

At block 720, the first data is examined, and a notification time associated with the voice message is determined. Block 720 may include, for example, using speech recognition techniques to identify a spoken time within the voice message itself or simply identifying a time value in a dedicated field of the first data.

At block 730, one or more speakers of the care receiver (e.g., speaker 154) is/are caused to generate the voice message at the notification time. In block 740, the care receiver's computing system is caused to listen for a response from the care receiver (e.g., via a microphone such as microphone 156). Block 730 and block 740 may both be executed by the act of transmitting the first data to the care receiver's computing system, for example, or by sending additional data (e.g., separate "playback" and "listen" commands) to the care receiver's computing system.

At block 750, a voice response is received from the care receiver's computing system. At block 760, second data that includes the voice response (e.g., second data 500) is sent to the computing system of the caregiver. In an alternative scenario, if no response is received from the care receiver's computing system before a message expire time (e.g., message expire time 406), then block 760 may instead include sending alarm data to the caregiver's computing system and/or another computing system (e.g., the computing system of a third party such as an emergency responder). As discussed above, multiple alarm levels may be supported, and/or different alarms may be routed to different parties.

Unless specifically stated otherwise, "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

As used herein, the terms "comprises," "comprising," "includes," "including," "has," "having" or any other variation thereof, are intended to cover a non-exclusive inclusion. Thus, whenever a claim employs any form of "include" or "comprise" (e.g., comprises, includes, comprising, including, having, etc.) As a preamble or within a claim recitation of any kind, it is to be understood that additional elements, terms, etc. May be present without falling outside the scope of the corresponding claim or recitation. As used herein, when the phrase "at least" is used as the transition term in, for example, a preamble of a claim, it is open-ended in the same manner as the term "comprising" and "including" are open ended.

Further, unless expressly stated to the contrary, "or" refers to an inclusive or and not to an exclusive or. For example, a, b or c refers to any combination or subset of a, b, c such as (1) a alone, (2) b alone, (3) c alone, (4) a with b, (5) a with c, (6) b with c, and (7) a with b and with c. As used herein, the phrase "at least one of a and b" is intended to refer to implementations including any of (1) at least one a, (2) at least one b, and (3) at least one a and at least one b. Similarly, the phrase "at least one of a or b" is intended to refer to implementations including any of (1) at least one a, (2) at least one b, and (3) at least one a and at least one b.

As used herein, the expressions "in communication," "coupled" and "connected," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, the term "non-transitory computer-readable storage media" is expressly defined to include any type of computer-readable storage device and/or storage disk and to exclude propagating signals and to exclude transmission media. As used herein, the term "non-transitory machine-readable media" is expressly defined to include any type of machine-readable storage device and/or storage disk and to exclude propagating signals and to exclude transmission media.

Any references, including publications, patent applications, and patents cited herein are hereby incorporated in their entirety by reference to the same extent as if each reference were individually and specifically indicated to be incorporated by reference and were set forth in its entirety herein.

Finally, unless a claim element is defined by reciting the word "means" and a function without the recital of any structure, it is not intended that the scope of any claim element be interpreted based on the application of 35 U.S.C. § 112, sixth paragraph.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed:

1. A method, implemented in a computing system of a care receiver, for sharing health care information, the method comprising:
receiving, via a network protocol, first data including a voice message from a computing system of a caregiver;
determining, by one or more processors of the computing system of the care receiver and based on the first data, a notification time associated with the voice message; and
causing, by the one or more processors, a speaker to generate the voice message at the notification time.

2. The method of claim 1, wherein the computing system of the care receiver receives the first data from the computing system of the caregiver via a computing system of a health care entity.

3. The method of claim 2, further comprising:
receiving, from the computing system of the health care entity, a list of one or more health care items that may assist the care receiver; and
causing, by the one or more processors, a speaker to generate a voice message comprising the list of one or more health care items.

4. The method of claim 2, further comprising:
receiving, from the computing system of the health care entity via the network protocol, health care information comprising marketing or medicinal information; and
causing, by the one or more processors, a speaker to generate a voice message indicating marketing information.

5. The method of claim 4, wherein receiving the medicinal information comprises receiving one or more of medication information, refill status, MD preauthorization information, vaccination information, potential drug interaction, health care appointment information, or insurance copay of the care receivers.

6. The method of claim 4, wherein receiving the marketing information comprises receiving one or more of: digital coupons, customer loyalty information, sale information or merchandise availability information.

7. The method of claim 4, further comprising:
causing, by the one or more processors, a speaker of the computing system of the care receiver to generate a voice message or messages with a request for an authorization to purchase one or more items;
receiving, via the microphone and from the care receiver, a voice authorization to purchase at least one of the one or more items; and
sending, to the computing system of the health care entity and via the network protocol, third data comprising the voice authorization.

8. The method of claim 1, further comprising:
receiving, from the care receiver via a microphone, a voice response message; and
sending second data including the voice response message to the computing system of the caregiver.

9. A method implemented in a computing system of a health care entity, the method comprising:
receiving, via a network protocol, first data from a computing system of a caregiver, the first data comprising a voice message;
determining a notification time based on the first data associated with the voice message; and
causing a speaker of a computing system of a care receiver to generate the voice message at the determined notification time, wherein causing the speaker to generate the voice message includes sending the voice message to the computing system of the care receiver.

10. The method of claim 9, further comprising:
determining from a voice response message of the care receiver a list of one or more health care items for the care receiver; and
sending to the computing system of the caregiver or to the computing system of the care receiver an indication of the list of one or more health care items.

11. The method of claim 9 further comprising:
receiving a location of the caregiver;
determining a proximity of the caregiver to a point of purchase; and
sending the list of one or more health care items for the care receiver to the caregiver based upon the proximity of the caregiver to the point of purchase.

12. The method of claim 9, further comprising:
examining a database comprising previous voice response messages and previously purchased items;
identifying a set of characteristics from a plurality of previously purchased items using previous voice response messages of other care receivers;
training a machine-learning model using (i) the set of characteristics and (ii) the previously purchased items;
determining, from a voice response message of the care receiver, one or more additional health care items for the care receiver, wherein determining the one or more additional health care items includes applying the voice response message to the machine-learning model to estimate which item or items may assist the care receiver; and
sending to the computing system of the caregiver or the computing system of the care receiver an indication of the one or more additional health care items.

13. The method of claim 12, further comprising:
sending, via the network protocol and to the computing system of the caregiver, marketing information including one or more of digital coupons, customer loyalty information, merchandise information or medicinal information;
prompting the computing system of the caregiver to authorize from the caregiver a purchase of one or more items; and
receiving from the computing system of the caregiver a fourth data comprising an authorization from the computing system of the caregiver to purchase at least one of the one or more items.

14. A non-transitory computer-readable storage media comprising instructions that, when executed by one or more processors of a computing system of a care receiver, cause the one or more processors to:
receive, via a network protocol, first data including a voice message from a computing system of a caregiver;
determine, based on the first data, a notification time associated with the voice message; and
cause a speaker to generate the voice message at the notification time.

15. The non-transitory computer-readable storage media of claim 14, wherein the instructions cause the one or more processors to receive the first data from the computing system of the caregiver via a computing system of a health care entity.

16. A non-transitory computer-readable storage media comprising instructions that, when executed by one or more processors of a health care entity, cause the one or more processors to:
    receive, via a network protocol, first data from a computing system of a caregiver, the first data comprising a voice message;
    determine, based on the first data, a notification time associated with the voice message;
    send the first data to a computing system of a care receiver; and
    cause a speaker of the computing system of the care receiver to generate the voice message at the notification time.

17. The computer-readable storage media of claim 16, wherein the instructions further cause the one or more processors to:
    determine, from a voice response message of the care receiver, a list of one or more health care items that may assist the care receiver; and
    send to the computing system of the caregiver or to the computing system of the care receiver an indication of the list.

18. The computer-readable storage media of claim 17, wherein the instructions further cause the one or more processors to:
    examine a database of previous voice response messages and previously purchased items;
    identify a set of characteristics of previously purchased items using previous voice response messages from a plurality of other care receivers;
    train a machine-learning model using (i) the set of characteristics and (ii) the previously purchased items;
    determine, from the voice response message of the care receiver, one or more additional health care items for the care receiver, wherein determining the one or more additional health care items includes applying the voice response message to the machine-learning model to estimate which item or items may assist the care receiver; and
    send to the computing system of the caregiver or the computing system of the care receiver an indication of one or more additional health care items.

19. The computer-readable storage media of claim 18, wherein the instructions cause the health care entity to:
    receive a location of the caregiver;
    determine a proximity of the caregiver to a point of purchase; and
    send the list of health care items for the care receiver to the caregiver based upon the proximity of the caregiver to the point of purchase.

20. The computer-readable storage media of claim 19 wherein the instructions further cause the one or more processors to:
    send, via the network protocol and to the computing system of the caregiver, marketing information including one or more of digital coupons, customer loyalty information, merchandise information or medicinal information;
    prompt the computing system of the caregiver to authorize a purchase of one or more items;
    cause the computing system of the caregiver to listen for a response from the caregiver; and
    receive, via the network protocol from the computing system of the caregiver, an authorization to purchase at least one of the one or more items on behalf of the care receiver.

* * * * *